United States Patent [19]

Henneke et al.

[11] Patent Number: 4,594,467

[45] Date of Patent: Jun. 10, 1986

[54] PREPARATION OF 3,5-DICHLORO-α-METHYLSTYRENE

[75] Inventors: Karl-Wilhelm Henneke; Herbert Diehl, both of Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 763,094

[22] Filed: Aug. 6, 1985

[30] Foreign Application Priority Data

Aug. 16, 1984 [DE] Fed. Rep. of Germany ....... 3430020

[51] Int. Cl.$^4$ .............................................. C07C 17/00
[52] U.S. Cl. .................................................. 570/193
[58] Field of Search ......................................... 570/193

[56] References Cited

U.S. PATENT DOCUMENTS 3,067,182 12/1962 Jones .................... 260/87.5
4,188,346 2/1980 Markley ................. 570/193
4,205,015 5/1980 Wang et al. ............. 570/193
4,230,642 10/1980 Nishiyama et al. ........ 570/193

Primary Examiner—Paul R. Michl
Assistant Examiner—Alex H. Walker
Attorney, Agent, or Firm—Sprung Horn Kramer & Woods

[57] ABSTRACT 3,5-Dichloro-α-methylstyrene is prepared from α-bromo-3,5-dichlorocumene by reaction with alkali metal hydroxide solutions in the presence of phase-transfer catalysts.

7 Claims, No Drawings

PREPARATION OF 3,5-DICHLORO-α-METHYLSTYRENE

The present invention relates to a process for the preparation of 3,5-dichloro-α-methylstyrene from α-bromo-3,5-dichlorocumene by reaction with alkali metal hydroxide solutions.

The dehydration, with acid catalysis, of 3,5-dichloro-α-hydroxycumene to give 3,5-dichloro-α-methylstyrene has been disclosed (see German Offenlegungsschrift No. 2,907,666 and European Offenlegungsschrift No. 27,155). It is a disadvantage of this process, apart from the unsatisfactory yield, that the starting material used is not readily available and can only be prepared expensively. According to German Offenlegungsschrift No. 2,907,666, it is possible to prepare 3,5-dichloro-α-hydroxycumene from 3,5-dichlorobromobenzene and acetone in a Grignard reaction. This synthesis can only be carried out in special apparatus with great elaboration for safety. European Offenlegungsschrift No. 27,155 describes a multistep route starting from 3,5-dichlorotoluene. After side-chain chlorination and hydrolysis, the resulting 3,5-dichlorobenzoic acid is esterified and subjected to a Grignard reaction with 2 moles of methyl magnesium chloride to give 3,5-dichloro-α-hydroxycumene. This process also can only be carried out with great industrial elaboration.

A variety of methods is known for the preparation of styrenes with other substituents. Thus, α-halogenoalkylbenzenes can be thermally cleaved to give the corresponding styrenes by distilling the starting material above 150° C. under reduced pressure (U.S. Pat. No. 3,067,182). Undesired side reactions, which reduce the yield, are disadvantageous with this process. Moreover, under the reaction conditions, large volumes of gaseous hydrogen halide have to be removed.

It has furthermore been disclosed that it is also possible using amines, such as pyridine and quinoline, to eliminate and bind the hydrogen halide from α-halogenoalkylbenzenes (Houben-Weyl, Methoden der organischen Chemie (Methods of Organic Chemistry), Volume V/1b, page 155 (1972)). It is a disadvantage of this process that the amines, which are used in molar amounts, have to be expensively regenerated for an economic process.

Recently, nuclear-substituted styrenes have been prepared by elimination of hydrogen bromide, carrying out the elimination in a multiphase system with sodium hydroxide solution in the presence of a phase-transfer catalyst. However, only substituted β-bromoethylbenzenes have been used in this process (Y. Kimura and S. L. Regen, J. Org. Chem. 1983, 195; U.S. Pat. No. 4,292,453; T. Nishikubo et al., Tetrahedron Letters 22, 3873 (1981); Jpn. Kokai Tokkyo Koho 79 132 529). This is remarkable to the extent that the possible preparation of β-bromoalkylbenzenes is generally more elaborate than that of the corresponding α-bromo derivatives. The latter are obtained by side-chain bromination of the corresponding alkylbenzenes, which is a proven and known method (see Houben-Weyl, Methoden der org. Chemie, Volume V/4, pages 331 et seq.).

A process for the preparation of 3,5-dichloro-α-methylstyrene by dehydrobromination of α-bromo-3,5-dichlorocumene has now been found, which is characterized in that α-bromo-3,5-dichlorocumene is reacted with alkali metal hydroxide solutions in the presence of phase-transfer catalysts above 70° C.

Suitable phase-transfer catalysts are quaternary ammonium compounds of the general formula (I)

in which
R$^1$ to R$^4$ are identical or different and represent alkyl groups having 1 to 20 C atoms, preferably 1 to 16 C atoms, which can be branched or unbranched, and/or represent benzyl groups which are unsubstituted or optionally substituted with lower alkyl and/or alkoxy groups and/or halogen atoms in the aromatic nucleus, and X represents a halogen atom, such as fluorine, chlorine, bromine or iodine, or the radical of an inorganic acid, such as bisulphate.

Examples of R$^1$ to R$^4$ which may be mentioned are: the methyl, ethyl, n-propyl, n-butyl, n-hexyl, dodecyl, hexadecyl, benzyl, p-chlorobenzyl and p-methoxybenzyl group.

Examples of phase-transfer catalysts which are preferably used in the process according to the invention and which may be mentioned are: triethylbenzylammonium chloride, tributylbenzylammonium chloride, hexadecyltrimethylammonium bromide and/or benzyldodecyldimethylammonium chloride.

Tetrabutylammonium bromide is particularly preferably used.

Other suitable phase-transfer catalysts are crown ethers and quaternary phosphonium salts as are described in Syntheses 1973, 441, and in Phase Transfer Catalysis, 2nd edition, Verlag Chemie, Weinheim.

The amount of phase-transfer catalysts used can vary within wide limits and is generally about 0.1 to 10 mol-%, preferably 0.5 to 1 mol-%, relative to α-bromo-3,5-dichlorocumene used.

The alkali metal hydroxide solutions, preferably sodium hydroxide solution, in the process according to the invention are advantageously used as concentrated aqueous solutions. The amount to be used is about 1 to 10 moles, preferably 1.2 to 3 moles, particularly preferably 1.5 to 2 moles, per mole of hydrogen bromide which is to be eliminated.

The reaction temperature is above 70° C., preferably about 80° to 110° C., particularly preferably at 100° to 110° C.

The charge stock α-bromo-3,5-dichlorocumene does not have to be used in the pure form. It is also possible to use crude α-bromo-3,5-dichlorocumene which is readily obtained by selective side-chain bromination of 3,5-dichlorocumene mixed with 2,4-dichlorocumene and/or 2,5-dichlorocumene (see U.S. Pat. No. 4,087,473).

In order to obtain high space/time yields, the reaction is preferably carried out without additional solvent. However, it is possible to use an inert solvent and/or diluent.

When α-bromo-3,5-dichlorocumene, tetrabutylammonium bromide and sodium hydroxide solution are used in the process according to the invention, then the course of the reaction can be represented by the equation below:

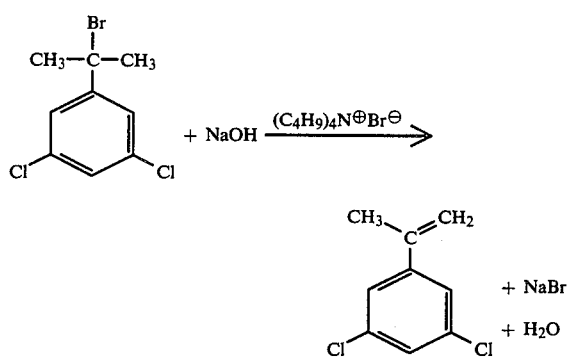

The process according to the invention can be carried out, for example, as follows:

α-Bromo-3,5-dichlorocumene, concentrated sodium hydroxide solution and the phase-transfer catalyst are initially introduced and heated, with stirring, to 100° to 110° C. To the mixtures which have reacted to completion is added sufficient water just to dissolve the precipitate of sodium bromide. The organic phase is separated off and the crude product is purified, depending on the purity required, by distillation through a distillation head and condenser or by fractional distillation.

It is also possible to meter the bromodichlorocumene wholly or partly at the reaction temperature into the sodium hydroxide solution and phase-transfer catalyst which have been initially introduced.

The process according to the invention is distinquished by several advantages compared with the state of the art. Using reasonably priced bases, it is possible to obtain 3,5-dichloro-α-methylstyrene in one straight-forward process step, in conventional vessel apparatus, from α-bromo-3,5-dichlorocumene which is readily available industrially. The yields are excellent and the selectivity is high.

3,5-Dichloro-α-methylstyrene is an intermediate for the preparation of plant-protection agents (see U.S. Pat. No. 4,211,548 and European Offenlegungsschrift No. 27,155).

The examples which follow are intended to explain the process according to the invention, without restricting it.

EXAMPLE 1

1,000 g of α-bromo-3,5-dichlorocumene (3.73 mol), 500 g of 45% strength sodium hydroxide solution (5.63 mol) and 10 g of tetrabutylammonium bromide were initially introduced into a 2 l three-neck stirring apparatus with reflux condenser and internal thermometer and, with vigorous stirring, first heated at 100° C. for 2 h and then at 110° C. for 6 h. The mixture was cooled slightly, about 500 ml of water were added, and the organic phase was separated off at about 50° C., the aqueous phase was extracted with about 300 ml of toluene, and the combined organic phases were distilled in vacuo. After toluene had been distilled off, 690 g of 99% pure 3,5-dichloro-α-methylstyrene were obtained as the distillate (yield 98% of theory).

EXAMPLE 2

1,000 g of crude, 81.7% pure (3.05 mol) α-bromo-3,5-dichlorocumene (obtained by bromination of a mixture of 78% 3,5-dichlorocumene and 20% 2,4-dichlorocumene in analogy to U.S. Pat. No. 4,087,473), 500 g of 45% strength sodium hydroxide solution and 10 g of tetrabutylammonium bromide were reacted and worked up as described in Example 1. 553 g of 99% pure 3,5-dichloro-α-methylstyrene were obtained by fractional distillation (yield 96% of theory).

EXAMPLE 3

500 g of 45% strength sodium hydroxide solution and 10 g of tetrabutylammonium bromide were heated to 100° C. in a 2 l four-neck stirred flask apparatus with reflux condenser, internal thermometer and dropping funnel. At this temperature, 1,000 g of crude, 81.7% pure α-bromo-3,5-dichlorocumene (see Example 2) were added dropwise in 1 h. After the addition, the temperature was raised to 110° C. and stirring was continued for 6 h. The mixture was worked up as described in Example 1 and, after fractional distillation, 549 g of 99% pure 3,5-dichloro-α-methylstyrene were obtained (yield 95% of theory).

EXAMPLE 4

1,000 g of crude, 71.3% pure (2.66 mol) α-bromo-3,5-dichlorocumene (obtained by bromination of a mixture of 67% 3,5-dichlorocumene, 18% 2,4-dichlorocumene and 13% 2,5-dichlorocumene in analogy to U.S. Pat. No. 4,087,473), 500 g of 45% strength sodium hydroxide solution and 10 g of tetrabutylammonium bromide were reacted and worked up as described in Example 1. After fractional distillation, 484 g of 99% pure 3,5-dichloro-α-methylstyrene were obtained (yield 96% of theory).

EXAMPLES 5 TO 8

The process is carried out in analogy to Example 1 but the phase-transfer catalysts which are indicated in the table were used. The yields were determined by gas chromatography analysis of the organic phase.

| Example | Catalyst | Amount[a] | Moles of NaOH[b] | Temp. °C. | Time h | Yield % of theory |
|---|---|---|---|---|---|---|
| 5 | Tetrabutyl-ammonium bromide | 1 | 1.2 | 100 | 8 | 95 |
| 6 | Benzyldo-decyldimethyl-ammonium chloride | 5 | 2 | 100 | 4 | 94 |
| 7 | Benzyltri-butylammonium chloride | 5 | 2 | 100 | 6 | 97 |
| 8 | Benzyltri-ethylammonium chloride | 1 | 10 | 85 | 4 | 99 |
| 9 | Benzyltri-ethylammonium chloride | 1 | 10 | 70 | 8 | 99 |
| 10 | Hexadecyltri-methylammo-nium bromide | 2 | 10 | 85 | 8 | 97 |
| 11 | 1,4,7,10,13,16-hexaoxacyclo-octadecane (18-crown-6) | 2 | 8.4[c] | 85 | 6 | 99 |

[a] % by weight relative to α-bromo-3,5-dichlorocumene
[b] 45% strength sodium hydroxide solution relative to α-bromo-3,5-dichlorocumene
[c] 50% strength potassium hydroxide solution It will be understood that the specification and examples are illustrative but not limitative of the present invention and that other embodiments within the spirit and scope of the invention will suggest themselves to those skilled in the art.

We claim:

1. In the preparation of 3,5-dichloro-α-methylstyrene by dehydrobromination of α-bromo-3,5-dichlorocumene, the improvement which comprises reacting the α-bromo-3,5-dichlorocumene with an alkali metal hydroxide solution in the presence of a phase-transfer catalyst above 70° C.

2. A process according to claim 1 wherein the phase-transfer catalyst is a quaternary ammonium compound of the formula

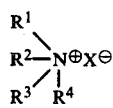

in which

R$^1$ to R$^4$ independently is an alkyl group having 1 to 20 C-atoms, or a benzyl group which is optionally substituted on the benzene ring by lower alkyl, lower alkoxy and/or halogen, and X is a halogen atom or the radical of an organic acid.

3. A process according to claim 1, wherein the phase-transfer catalyst is benzyldodecyldimethylammonium chloride, tributylbenzylammonium chloride, triethylbenzylammonium chloride, hexadecyltrimethylammonium, bromide and/or tetrabutylammonium bromide.

4. A process according to claim 1, wherein the phase-transfer catalyst is used in 0.1 to 10 mol-% relative to α-bromo-3,5-dichlorocumene.

5. A process according to claim 1, wherein the alkali metal hydroxide is sodium hydroxide.

6. A process according to claim 1, wherein 1 to 10 moles of alkali metal hydroxide are used per mole of hydrogen bromide which is to be eliminated.

7. A process according to claim 1, wherein the reaction temperature is 80° to 110° C.

* * * * *